(12) United States Patent
Horner et al.

(10) Patent No.: US 6,492,639 B1
(45) Date of Patent: Dec. 10, 2002

(54) METHOD AND APPARATUS FOR RECOGNIZING PROPERTIES OF A SAMPLE BASED ON MASS SPECTROSCOPY

(75) Inventors: Gerhard Horner, Wolfratshausen (DE); Siegfried Nitz, Eching-Weixerau (DE); Brigitte Dittman, Munich (DE); Harun Parlar, Zolling (DE)

(73) Assignee: HKR Sensorsysteme GmbH, Munich (DE)

( * ) Notice: Subject to any disclaimer, the term of this patent is extended or adjusted under 35 U.S.C. 154(b) by 0 days.

(21) Appl. No.: 09/381,932
(22) PCT Filed: Mar. 16, 1998
(86) PCT No.: PCT/DE98/00762
  § 371 (c)(1),
  (2), (4) Date: Sep. 27, 1999
(87) PCT Pub. No.: WO98/44536
  PCT Pub. Date: Oct. 8, 1998

(30) Foreign Application Priority Data

Mar. 27, 1997 (DE) .......................... 197 13 194

(51) Int. Cl.[7] ............. B01D 59/44; H01J 49/00
(52) U.S. Cl. ......................... 250/282; 250/281
(58) Field of Search ............... 250/282, 281, 250/283

(56) References Cited

U.S. PATENT DOCUMENTS 4,507,555 A * 3/1985 Chang ................... 250/282
5,247,175 A * 9/1993 Schoen et al. ............ 250/282
5,352,891 A * 10/1994 Monnig et al. .......... 250/282
5,545,895 A * 8/1996 Wright et al. ............ 250/282
6,008,490 A * 12/1999 Kato ...................... 250/282

FOREIGN PATENT DOCUMENTS

| JP | 07320682 A | * 5/1994 |
| WO | WO 90 07326 | 4/1992 |
| WO | WO 92 13315 | 8/1992 |

OTHER PUBLICATIONS

Ragunathan N. et al., "Multispectral Detection for Gas Chromatography", Journal of Chromatography, vol. 703, No. 1, May 26, 1995, pp. 335–382.
Keller P E et al, "Electronic Noses and Their Applications", IEEE Technical Applications Conference and Workshops at Northcon '9, Portland, Oct., 1995.
Newman, "Electronic Noses", Analytical Chemistry, vol. 63, No. 10, May 15, 1991.

* cited by examiner

Primary Examiner—Bruce Anderson
(74) Attorney, Agent, or Firm—David Aker

(57) ABSTRACT

The invention relates to a method and device enabling time-saving, comparative mass spectrometric analysis of serial samples corresponding to a reference, for example serial samples of a product, by conditioning by means of a reference sample and forming a pattern of a reduced number of fragment ions, said fragment ions having selected from individual mass spectrums of the same separated by gas chromatography, and forming a pattern of a reference random sample from overall mass spectrograms of several reference samples reduced accordingly.

20 Claims, 2 Drawing Sheets

METHOD AND APPARATUS FOR RECOGNIZING PROPERTIES OF A SAMPLE BASED ON MASS SPECTROSCOPY

FIELD OF THE INVENTION

The present invention relates to a method for recognizing properties of a material that are of interest, based on the volatile and/or vaporizable portions of this material. The invention is used in particular to be able to make comparisons of materials/substances basically considered identical/similar, in order to recognize whether there are actually differences between these compared substances with respect to the concerned properties. A specific field of application is the food sector, for example, in order to be able to make quality categorizations of batches thereof.

BACKGROUND ART

It is known that in organic chemical analysis, mass spectrometry is the most important detection method for identifying unknown individual substances.

In particular the combination of mass spectrometric detection with static headspace gas chromatography is a well-established routine analysis method for qualitative and quantitative determining of the volatile components of an unknown sample. This method of analysis is based on the fact that in a closed container, the very volatile and moderately volatile components of a sample spread out between the sample matrix and the gaseous phase over this matrix. In this connection, the sample matrix itself may be liquid or solid. In the state of thermodynamic equilibrium, the gaseous phase contains a qualitatively and quantitatively representative equivalent of all volatile components. For this reason, for identifying the volatile components of an unknown sample, a defined gas volume, what is referred to as the aliquot, is removed from the gaseous phase and is fed to the gas chromatographic separation with subsequent mass spectrometric detection.

It is known to use static headspace gas chromatography in combination with mass spectrometry in different areas of organic chemical analysis.

It is known from Ragunathan, N. et al. "Multispectral detection for gas chromatography" JOURNAL OF CHROMATOGRAPHY A, vol. 703, no. 1, 26th May 1995, pp. 335–382 XPOO4023371, to timewise separate an unknown mixture of substances into its single components, which can be sequentially analyzed by a mass spectrometer. For each single component an individual mass spectrum can be recorded within a respective time window. In the following spectral analysis the individual mass spectrum of each single component is compared to a given catalogue (library) containing the mass spectra of various reference substances. To reduce library search time the system selects only a few ionized fragments from the individual mass spectrum to be compared with the reference spectra by introducing a threshold for the minimum peak height. The intensity of the spectral line determines which spectral lines are used for the spectral comparison. The system selects only a reduced number of spectral lines for evaluation.

From Belitz and Grosch, "Lehrbuch der Lebensmittelchemie" [Textbook of Food Chemistry] (1992), p. 312, it is known that this method of analysis, known under the acronym HSGC/MS, is well-established in particular in the food industry sector, because the type as well as the number of volatile components contained in a food sample are of decisive significance for the quality of a food. In particular the presence of certain odor-active volatile components that mark the aroma of a food sample, and their concentration in the food sample, are used in this connection as the basis for quality assessment.

Likewise, in numerous sectors of environmental analysis, in particular in utilization of waste products, in environmental monitoring, in emission studies of packaging material and in emission analysis, the routine decoding of the volatile components of a sample to be examined takes place by means of the HSGC/MS method. In this case as well, the odor-active volatile components are particularly significant because they are used to assess the annoyance of emissions. HSGC/MS analysis has similar importance for determining maximum workplace concentration values.

From Newman, "Electronic Noses", Analytical Chemistry 63 (10), pp. 585A–588A, it is known that in recent times, in particular in the field of food quality control, instruments that are referred to as "electronic noses" are used for the objective, rapid measuring/characterization of odors. These are sensor arrays of several unselective individual sensors that are housed together in a measuring chamber. Just as in HSGC/MS analysis, the "sample" arriving for measuring is an aliquot of the gaseous phase that is situated above the actual liquid or solid sample matrix. The individual signals delivered by the individual sensor elements when volatile substances are present in the gaseous phase are evaluated by methods of pattern recognition, known from Gardner and Bartlett, Sensors and Sensory Systems for an Electronic Nose (1992), p. 161. In this connection, cluster analysis in the multidimensional space or neural networks are preferably used.

In particular when studying odorous samples with the help of sensor arrays, there is no identification of the volatile components contained in the sample. For this reason, neither the components decisive for the odor of the sample nor the odorless components become known thereby. If two odorous samples differ only in that non-odor-active components are present in different concentrations, both samples are classified as different by the "electronic nose", although they are assessed identically in human sensory perception. Such an erroneous classification limits the ability of "electronic noses" to be used universally.

In practical experience, in particular in the food sector, the technical problem that is often presented is to recognize materials, e.g. from batches, goods deliveries and the like in order, for example, to be able to carry out a quality classification thereof, or to allow evaluation comparisons between substances considered identical/similar, where this supposed parity actually does not hold true. A simple example is provided not for limitation, but rather only as an illustration. Different batches, e.g., of parsley delivered should actually be of uniform quality. For example, these batches cannot be differentiated optically from each other, yet they display odor differences. The recognition to be executed with the invention is intended to allow objective differentiation of the individual batches, for example for the purpose of classification into merchandise categories.

A technical problem addressed by of the present invention is to indicate a method that makes such recognition or differentiation executable at the least possible expense and in particular in a brief time.

This technical problem is solved with the teachings of patent claim 1, and in further developments according to the subclaims.

The invention is based on basically known recording and evaluation of mass spectra of complex substance mixtures, but including, according to the invention, measures that allow mass spectrometry, familiar in principle, to be applied in a simplified manner in that a given (random) reference sample is taken as a basic pattern, and the actual series of tests are conducted only as comparisons with simplified expenditure. In particular, when examining and evaluating the individual (series) samples of the testing series, the method according to the invention does so without conducting gas chromatographic separation of the components of these samples in each case, namely without loss of quality or general validity of the (quality) assessment achieved.

The method according to the invention has the advantage that in (merchandise) classification not every individual sample is to be examined in detail in a time-consuming manner. Rather, as is also shown more thoroughly in the following detailed description, only a one-time calibration procedure is carried out with a (random) reference sample for this merchandise, namely preferably with an arrangement also to be used for conducting the subsequent series tests, as is described in FIG. 2, for example.

With respect to a pattern analysis/evaluation used with the invention, the following should be noted:

A pattern (of a sample) relevant in this case comprises a number n of pattern values which, taken together, are to be considered an n-dimensional vector in the n-dimensional space and form the pattern. Two patterns concurring signifies that the vector of one pattern and the vector of the other pattern concur in length and direction. For the practical execution of pattern analysis, however, it is necessary to take into account/ predetermine a tolerance space depending on the technical problem/requirement for such a concurrence. That means that the concurrence of two or more patterns already exists when the tip of the vector of the given pattern is situated within this n-dimensional tolerance space (provided that the vectors have a concurring point of origin).

An individual pattern with n pattern values is obtained when one determines from a (first) reference sample the number n of predetermined characteristic values thereof. If one examines a seemingly identical second reference sample which, as is typical in practical reality, is only nearly identical to the first reference sample, a second, only nearly identical pattern is obtained. Several such reference patterns taken together lead to or form in this case (according to a first variant for execution of the invention) a reference random sample for which there accordingly results a random sample pattern of values objectively determined and/or taking tolerances into account; this random sample pattern is to be considered a vector with the tolerance range of its length and its direction (=tolerance space). This is synonymous with the term (reference) random sample pattern for this variant. A second variant is to determine and/or set such a tolerance space for the reference random samples e.g. from experience (experimental values), derived from requirements of the technical problem and the like. For this, only one reference sample is then needed for the pattern vector as the one to which, for the characteristic of serving as reference sample pattern, the predetermined tolerance is thus (subjectively) assigned.

Here it should be briefly noted that according to the invention with (at least) one selected reference sample and one reference random sample, this is formed (according to the first variant) from a representative selection of reference samples in statistically sufficient number or (according to the second variant) with a predetermined tolerance space, a testing measure belonging to the invention is conducted in two phases, in order to create, for this reference random sample with its tolerance space of its pattern vector and for the series tests e.g. of the merchandise batches to be conducted subsequently, a pattern, as also described in more detail, adapted to the technical problem and with only a limited number of ionized fragments of the volatile components of the reference random sample.

In the first phase of this testing measure, from (at least) one reference sample the mass spectra of the individual substance components (of interest) are determined separately from each other by gas chromatography. In this connection, each such individual mass spectrum of a single substance component contained in the reference sample consists of 50 to 250 ionized fragments, for example.

It is basically sufficient in this first phase to record, as indicated, the individual mass spectrum of only a single selected reference sample to save time and money. To completely rule out the possibility that a perhaps less pertinent selection of this single reference sample could lead to a perhaps less favorable result to be achieved with the invention, it may be useful to record in this first phase the respective individual mass specta of several selected reference samples (required in the subsequent second phase for the above first variant).

For the practical reality of a pattern recognition analysis solving the technical problem, such a number of ionized fragments of the individual components of the sample is already too great to take them all into consideration. For this reason, the invention provides, by mass spectrometry in the second phase of the testing measure, for continued detection and evaluation as pattern values of only a reduced number (described below) of selected ionized fragments, e.g. 10, namely of the overall mass spectrum of the unseparated reference sample (in which all individual parts of the sample are thus contained). This reduced number of ionized fragments/pattern values then also serves as the basis for the pattern recognition analysis of the—according to the technical problem of the present invention—brief series testing of batches/series samples that are to be compared in each case with the pattern or (as in this case for two variants) with the reference random sample pattern defined.

One selects form these individual mass spectra of the first phase those ionized fragments that occur particularly specifically and/or quite dominantly in the respective individual mass spectrum of volatile content substance/substance component and/or are an indication/characteristic for the particular property /quality of the entire reference random sample to be formed. According to the second phase, a reduced mass spectrum is taken of each undivided reference sample of the reference random sample, which consists of only the 20 ionized fragments, for example (determined in the described manner). Thus, no gas chromatography breakdown of the reference samples is carried out in this second phase. Depending on the property/quality that is to be recognized, a weighting of the relevant ionized fragments in the pattern recognition process can then still be carried out.

The above-described recommendation to record the individual mass spectra of more than just one reference sample then apparently serves to obtain a particularly optimally pertinent selection of the ionized fragments uses in reduced number for the further pattern comparison.

The following comparison of the reduced overall mass spectra determined in each case by the individual, unseparated samples of the batches of the series test with the pattern of the reference random sample is carried out by means of a pattern analysis based on the weighted, selected ionized fragments, e.g. 20 such weighted ionized fragments are evaluated.

This summary shows that the actually time-consuming phase of mass spectrometric examination with gas chromatographic breakdown into portions of the content substances of a sample only has to be carried out once and (usually) only for one reference sample.

A further simplification for a further development of the invention results, for example, from drawing up catalogues of the patterns, consisting of the weighted reduced mass spectra of the reference random samples for various substances, e.g. various types of vegetable, fruit and the like; these catalogues are used repeatedly when new goods are delivered in order for the comparison to be made according to the invention. In this connection, as described above, for the samples of the series tests in each case only the respective reduced overall mass spectrum of this merchandise sample then needs to be recorded and evaluated, namely without gas chromatographic breakdown of the merchandise samples.

BRIEF DESCRIPTION OF THE DRAWINGS

In the following, the procedure according to the invention is also explained in greater detail by means of an example of execution and the equipment used.

DETAILED DESCRIPTION OF THE PREFERRED EMBODIMENTS

Figure 1:
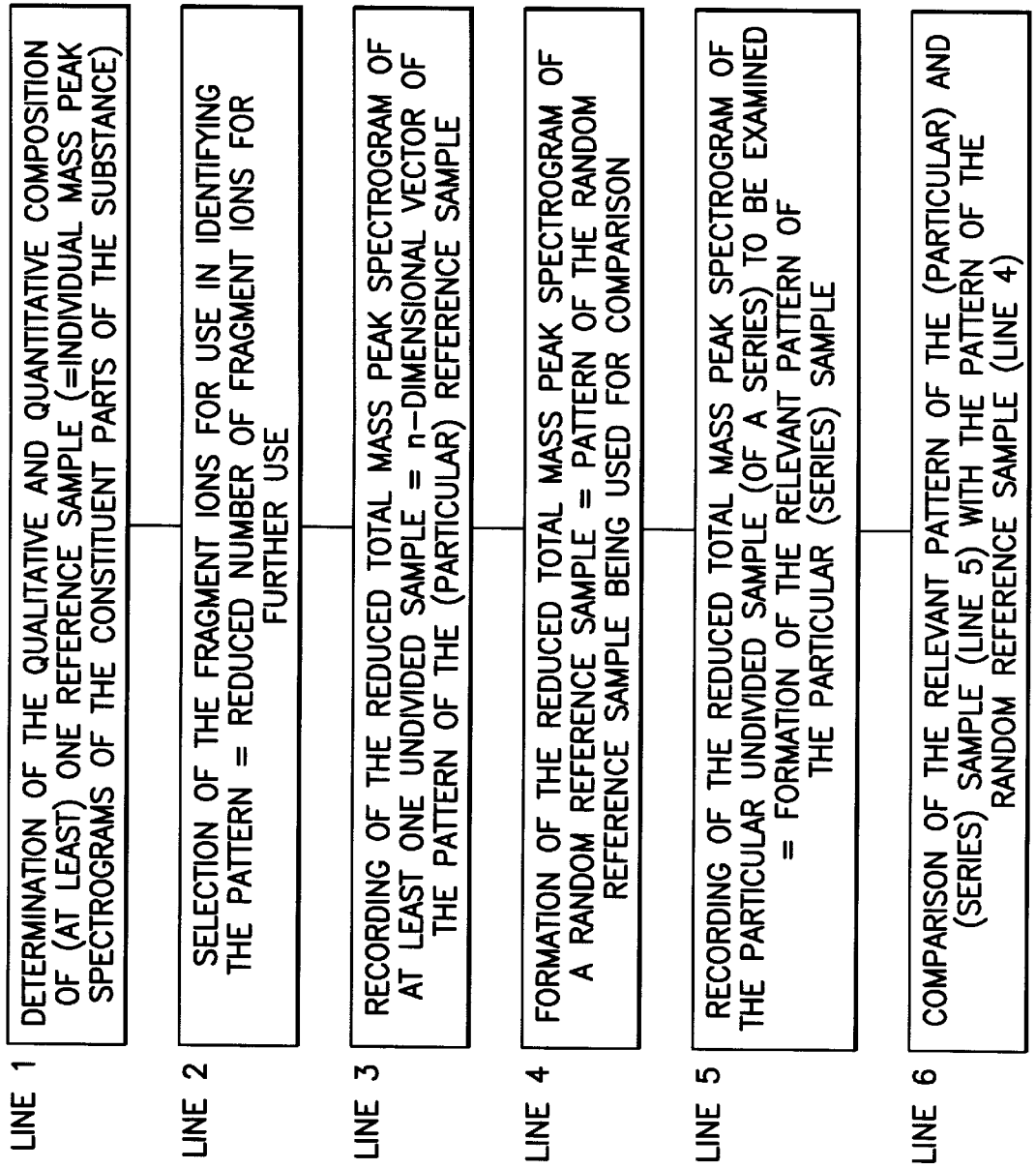
FIG. 1 shows a diagram of the progression of a method executed according to the invention.

FIG. 1 shows the method according to the invention as a flow chart. The first four lines 1, 2, 3 and 4 concern the above-described measures for testing the arrangement, also according to the invention, of the (at least) one reference sample (lines 1 and 2) and the reference random sample (lines 3 and 4). These measures are to be carried out once for all subsequent tests. The fifth line of FIG. 1 concerns these subsequent mass spectrometric tests of serial samples to be evaluated (in assigned manner) which are to be examined by order. The sixth line of FIG. 1 concerns the comparison of the respectively examined sample of the step of the fifth line with the testing result of the fourth line of FIG. 1, namely with the pattern of the reference random sample.

Figure 2:
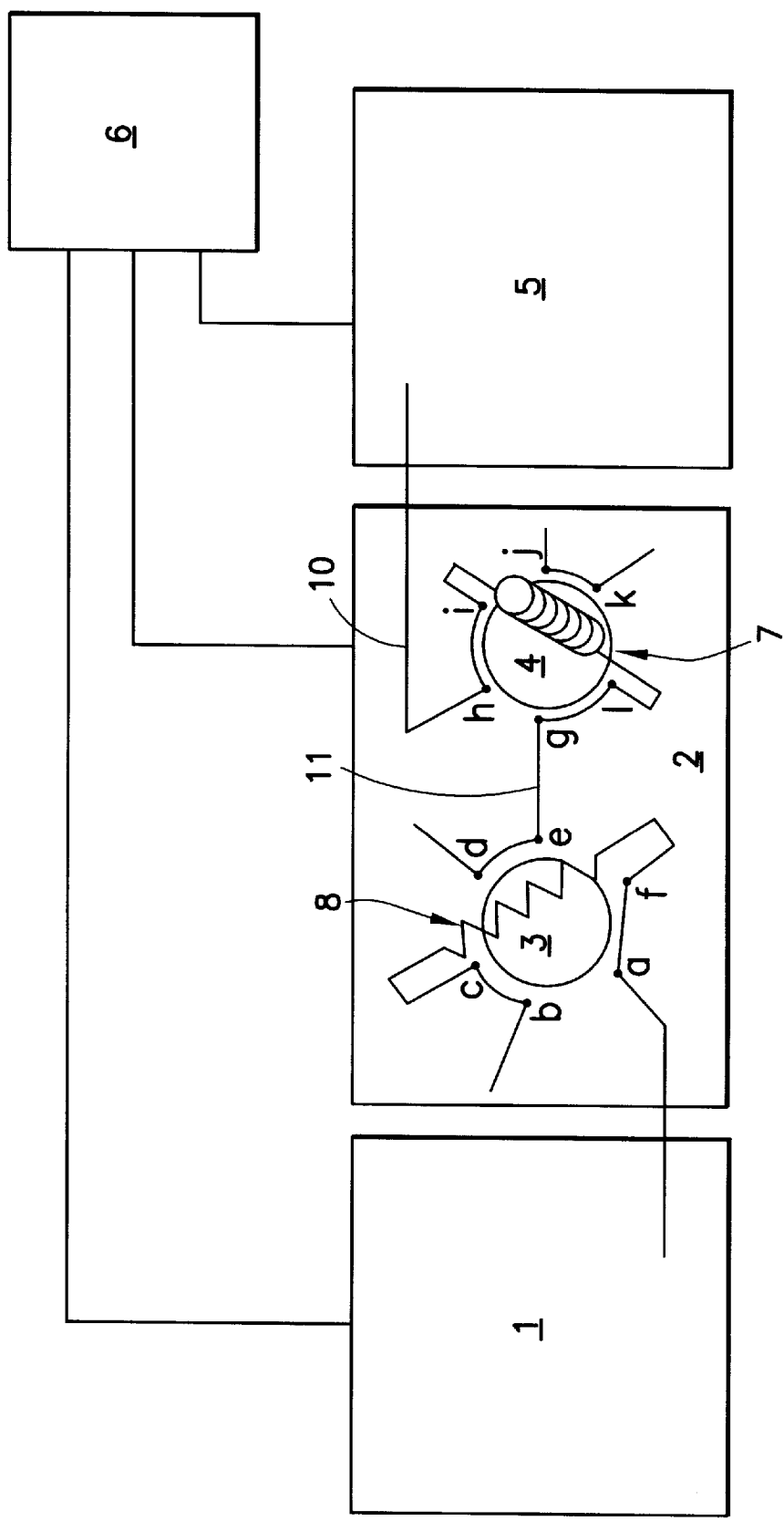
FIG. 2 shows a possible setup of an arrangement for executing this method.

The arrangement according to FIG. 2 comprises a headspace sampling system 1, as already described above in principle and basically known, a basically known gas chromatograph 2 with a first 6-port valve 3 and a second 6-port valve 4 that are arranged in the furnace space of the gas chromatograph, a mass spectrometer 5 and a personal computer 6.

The port c and the port f of the first 6-port valve 3 are joined together by means of a sample loop 8. The port a is connected with the headspace sampling system 1, whereby this connection is a fused silica capillary or a stainless steel capillary, for example. Connected to port 1 and port 1 of the second 6-way valve 4 is the respective one of the two ends of a gas chromatography column 7. The first 6-port valve 3 and the second 6-port valve 4 are joined together via a first capillary 11. For this, one end of this connection is connected with the port e of the first 6-port valve 3 and the other end of this connection is connected with the port g of the second 6-port valve 4. A feed tube for inert gas is connected to the port j of the second 6-port valve 4. The ports b and k of the respective 6-port valve are intended as gas connections for flushing purposes.

The second 6-port valve 4 and the mass spectrometer 5 are joined together, and this connection contains a second capillary 10, a restriction capillary.

The chromatograph 2 as well as the mass spectrometer 5 can be controlled with signals from a personal computer 6. The data to be obtained are also evaluated with this personal computer, for example.

For the sample feed, the use of the above-mentioned static headspace technique is preferably provided for, in connection with which the respective sample to be examined is already located in a tightly closed sample container before the beginning of the analysis.

In a first step of a first phase of testing measure of the method according to the invention, predetermined reference sample is brought to an optionally preset sample pressure for a period that can be freely preselected by the user. It is incubated at a constant, likewise optionally predetermined temperature. At the end of the equilibration phase, the state of thermodynamic equilibrium is achieved. In the gaseous phase that is then present over the sample matrix, a representative equivalent of all very volatile and moderately volatile compounds originally contained in the reference (sample) are present. These compounds are odor-relevant compounds as well as compounds that do not contribute to the odor of the sample.

In the second step of this first phase of testing, a volume of the gaseous phase to be measured is released in the sample loop 8 that has a defined volume. This sample loop connected with the first 6-port valve 3 is then located in the furnace space of the gas chromatograph 2. By switching the first 6-port valve 3, the gaseous phase to be measured is then forwarded to the second 6-port valve 4.

In terms of equipment, the gaseous phase to be measured may optionally be forwarded into the mass spectrometer 5 directly or via the gas chromatography column 7 which is designed identical to the loop 8, for example. The first 6-port valve 3 and the second 6-port valve 4 are controlled by the gas chromatograph 2 for purposes of dosing and/or forwarding of the sample.

The input of the (reference) sample to be measured via the gas chromatography column 7 into the mass spectrometer 5 thus creates the conditions for the quantitative and qualitative analysis of all odor-relevant components of this substance by means of their mass spectra.

A direct feeding-in of a sample (past the gas chromatography column 7) into the mass spectrometer 5 results in the recording, described below, of an overall spectrum of the respective, thus unseparated and now gaseous, sample. As the second phase of the testing measure, this recording of the overall spectrum (also) takes place for the reference sample.

The respective sample can be fed directly from the sampling system into the mass spectrometer by means of direct coupling. Alternatively, this can be done by means of the well known coupling technique of "open split" coupling between sampling system and mass spectrometer.

Thus, the two phases of the testing of the reference sample provide on the one hand the above-mentioned individual spectra of the individual volatile portions of reference sample and, on the other hand, the overall spectrum thereof The evaluation of these spectra of the reference sample with limitation of the ionized fragments is already described above. This is a high-dimensional signal array that can be (further) processed by means of known signal processing methods (discrimination analysis, neural networks). With the help of the above-described testing, the arrangement according to the invention is prepared to an extent that it can be used to carry out the analytical measurements of a series of samples whose characteristics are to be determined. The ionized fragments of the sample to be examined, determined using the arrangement according to the invention, are separated and are compared as obtained signal patterns with the reference pattern that was obtained by means of the testing. One can then evaluate the differences that are to be determined between the respective sample to be examined and the reference random sample. With the help of the arrangement according to the invention, the respective measurement of the unknown sample can be carried out using only brief cycle times.

According to this method of the invention, in particular for a number of samples to be examined, the difference in the complex composition of the individual samples compared to the reference can be determined in a brief time.

The output of a sensor array is highly dependent on the optimal sensor combination. With conventional sensor arrays with a fixed sensor combination, an optimization of pattern recognition is possible only in a very limited manner. As a rule, this can only be achieved by replacing or changing the arrays. On the other hand, the method according to the invention distinguishes itself in that the adaptation to the sample to be assessed does not require any changing of the array hardware. The optimal adaptation takes place by taking into account the data, determined in the testing, on the qualitative and quantitative composition of (at least) one representative reference sample with respect to the property/quality to be recognized. The ionized fragments necessary for optimal discrimination of the sample are determined from the individual spectra of the substances contained in the reference sample(s). For this reason, the type and number of ionized fragments that are necessary for an optimal discrimination of the sample are flexibly adapted to the given classification problem.

Another advantage consists in the ability of the method according to the invention to be standardized and to be transferred to similar arrangements consisting of a headspace sampling system, a gas chromatograph and a mass spectrometer, similar to the described arrangement according to the invention. Regardless of the type of arrangement used for the measurement, the comparability of the classification results form the measurement is ensured by means of different arrangements, because in all cases identical measuring values, namely ionized fragments and their intensity, are used as the basis for sample recognition analysis. Such a transferability of the results is only possible to a limited extent with chemical sensor arrays, because most "electronic noses" differ in the type of measuring signal evaluated in the pattern recognition analysis.

A further advantage that the arrangement according to the invention has compared to chemical sensor arrays consists in the better reproducibility of the results. Unlike chemical sensors which, depending on the type of the respective sensors, are subject to more or less considerable symptoms of aging such as zero drift, the arrangement according to the inventions shows no such symptoms of aging.

What is claimed is:

1. A method for recognizing the deviation of characteristics of a sample from those of a reference, executed by comparing mass spectrometric patterns of the respective sample with the reference, comprising:

determining an overall mass spectrum from at least one reference random sample selected for a reference, forming a reduced mass spectrum with related tolerance space from this overall mass spectrum of this reference random sample, determining a reduced mass spectrum from the sample to be compared with the reference random sample, and comparing the reduced mass spectrum of the sample with that of the reference random sample to determine whether the reduced mass spectrum is within the related tolerance space.

2. The method according to claim 1, further comprising:

determining from at least one selected reference sample the respective individual mass spectra of substance portions of this/these reference sample/s separated from each other by gas chromatography, and selecting from these individual mass spectra a reduced number of those type of ionized fragments that were determined from these individual mass spectra to be valued as characteristic/dominant for such a reference sample.

3. The method according to claim 1, wherein at least one of individual and overall mass spectra of only a single selected reference sample are determined.

4. The method according to claim 1, wherein the tolerance space related to the reference random sample pattern formed from only one reference sample is determined in a standardizable manner.

5. The method according to claim 1 further comprising:

selecting for the tolerance space related to the reduced mass spectrum of the reference random sample, a representative selection of several reference samples in statistically sufficient number, from which the respective reduced overall mass spectra are determined and from these taken together, the reduced overall mass spectrum of the reference random sample with its related tolerance space is formed.

6. The method according to claim 1, wherein for the repeated comparing of series samples of a single type of good, the pattern of a reference random sample is used as a standard.

7. The method according to claim 1, further comprising:

creating for different types of the respective series samples, a catalogue of patterns of respectively assigned reference random samples, corresponding to the number of these types.

8. The method according to claim 1, wherein the reduced mass spectrum of the reference random sample with related tolerance space is determined from a catalogue.

9. The method according to claim 1, further comprising:

obtaining the sample by means of static headspace sampling.

10. The method according to claim 1, further comprising:

selecting the type and number of mass lines used for pattern recognition analysis according to a HSGC/MS calibration measurement.

11. The method according to claim 1, further comprising:

feeding the sample directly from a sampling device into the mass spectrometer by direct coupling.

12. The method according to claim 1, further comprising:

feeding the sample directly from a sampling device into the mass spectrometer by open split coupling.

13. An apparatus for carrying out a method for recognizing the deviation of characteristics of a sample from those of a reference, executed by comparing mass spectrometric patterns of the respective sample with the reference, the method including, determining an overall mass spectrum from at least one reference random sample selected for a reference, forming a reduced mass spectrum with related tolerance space from this overall mass spectrum of this reference random sample, determining a reduced mass spectrum from the sample to be compared with the reference random sample, and comparing the reduced mass spectrum of the sample with that of the reference random sample to determine whether the reduced mass spectrum is within the related tolerance space, the apparatus comprising two 6-port valves (3,4) that are connected with each other in the furnace of a gas chromatograph (2).

14. The apparatus according to claim 13, wherein a gas chromatograph column (8) is attached to a second of the 6-port valves (4).

15. The apparatus according to claim 13, configured so that material of the samples can be directed optionally via gas chromatographic separation or unseparated, directly to the mass spectrometer.

16. The apparatus according to claim 13, further comprising a sampling device connected directly with the mass spectrometer.

17. A method for recognizing the deviation of characteristics of a sample from those of a reference, executed by comparing mass spectrometric patterns generated by a mass spectrometer of the respective sample with the reference, comprising:

determining an overall mass spectrum of the reference, forming a reduced mass spectrum from this overall mass spectrum of the reference, determining a reduced mass spectrum of the sample to be compared with the reference, and comparing the reduced mass spectrum of the sample with that of the reference, wherein the reference and the sample are directly injected from a sampler into the mass spectrometer.

18. The method according to claim 17, wherein direct injection is performed through one of an open coupling or a direct coupling.

19. An apparatus for carrying out a method for recognizing the deviation of characteristics of a sample from those of a reference, comprising:

a sampling device for taking samples;

a mass spectrometer;

an analyzer associated with said mass spectrometer for determining a reduced mass spectrum of said reference, for determining a reduced mass spectrum of the sample to be compared with the reference, and for comparing the reduced mass spectrum of the sample with the reduced mass spectrum of the reference, and a connection for connecting the sampling device directly with the mass spectrometer.

20. The apparatus according to claim 19, wherein said connection comprises one of an open coupling or a direct coupling.

* * * * *